(12) United States Patent
Mathuis et al.

(10) Patent No.: US 9,904,248 B2
(45) Date of Patent: Feb. 27, 2018

(54) DIGITAL HOLOGRAPHIC MICROSCOPE WITH FLUID SYSTEMS

(71) Applicant: OVIZIO IMAGING SYSTEMS NV/SA, Brussels (BE)

(72) Inventors: Philip Mathuis, Brussels (BE); Serge Jooris, Brussels (BE)

(73) Assignee: Ovizio Imaging Systems NV/SA, Brussels (BE)

( * ) Notice: Subject to any disclaimer, the term of this patent is extended or adjusted under 35 U.S.C. 154(b) by 313 days.

(21) Appl. No.: 14/429,616

(22) PCT Filed: Sep. 20, 2013

(86) PCT No.: PCT/EP2013/069625
§ 371 (c)(1),
(2) Date: Mar. 19, 2015

(87) PCT Pub. No.: WO2014/044823
PCT Pub. Date: Mar. 27, 2014

(65) Prior Publication Data
US 2015/0248109 A1    Sep. 3, 2015

(30) Foreign Application Priority Data

Sep. 20, 2012    (EP) .................................... 12185229

(51) Int. Cl.
*G02B 21/00*    (2006.01)
*G03H 1/00*    (2006.01)
(Continued)

(52) U.S. Cl.
CPC ........ *G03H 1/0005* (2013.01); *B01L 3/50273* (2013.01); *B01L 3/502715* (2013.01);
(Continued)

(58) Field of Classification Search
CPC ............. G03H 1/0005; B01L 3/502715; B01L 3/50273
(Continued)

(56) References Cited

U.S. PATENT DOCUMENTS 4,786,594 A    11/1988 Khanna et al.
5,089,416 A    2/1992 Schwartz
(Continued)

FOREIGN PATENT DOCUMENTS

CN    202 808 799    3/2013
EP    0479231 A1    4/1992
(Continued)

OTHER PUBLICATIONS

Fook Chiong Cheong, Flow visualization and flow cytometry with holographic video microscopy, Practical Holography XXIV: Materials and Applications, 2010, in 6 pages; vol. 7619, SPIE.
(Continued)

*Primary Examiner* — Bumsuk Won
*Assistant Examiner* — Tamara Y Washington
(74) *Attorney, Agent, or Firm* — Knobbe Martens Olson & Bear, LLP

(57) ABSTRACT

The current invention concerns a fluid microscope system for analyzing and/or monitoring the contents of one or more fluid-based reactors or canalizations such as bio-reactors, micro-reactors, brewing reactors, water supply systems or sewer systems comprising a digital holographic microscope (DHM) capable of obtaining phase information of a fluid sample and comprising illumination means and one or more fluidic systems connected to said reactors and to said DHM, capable of guiding fluid from said reactors to said DHM, whereby at least one fluidic system comprises one or more tubes which may come in direct contact with fluid from said reactor, characterized in that at least one tube comprises a
(Continued)

part which is at least partially transparent for the illumination means of said DHM for obtaining holographic information of said fluid sample. The current invention also concerns a tube and a fluidic system for such a fluid microscope.

20 Claims, 9 Drawing Sheets

(51) Int. Cl.
    *G03H 1/04*     (2006.01)
    *C12M 1/34*     (2006.01)
    *G02B 21/26*     (2006.01)
    *G03H 1/02*     (2006.01)
    *B01L 3/00*     (2006.01)

(52) U.S. Cl.
    CPC ......... *C12M 41/36* (2013.01); *G02B 21/0016* (2013.01); *G02B 21/26* (2013.01); *G03H 1/0443* (2013.01); *B01L 3/5027* (2013.01); *B01L 2200/025* (2013.01); *B01L 2200/143* (2013.01); *B01L 2300/0654* (2013.01); *B01L 2300/088* (2013.01); *B01L 2300/0864* (2013.01); *B01L 2300/0877* (2013.01); *B01L 2300/123* (2013.01); *B01L 2300/168* (2013.01); *B01L 2400/0481* (2013.01); *G03H 2001/005* (2013.01); *G03H 2001/0204* (2013.01)

(58) Field of Classification Search
    USPC .................................................. 359/362–372
    See application file for complete search history.

(56) References Cited

U.S. PATENT DOCUMENTS

| | | | |
|---|---|---|---|
| 5,243,409 A | 9/1993 | Sagner | |
| 5,256,571 A | 10/1993 | Hurley et al. | |
| 5,495,333 A | 2/1996 | Konda | |
| 6,249,345 B1 | 6/2001 | Kraack | |
| 6,327,377 B1 | 12/2001 | Rutenberg | |
| 6,361,934 B1 | 3/2002 | Acton | |
| 6,394,966 B1 | 5/2002 | Gill | |
| 6,651,008 B1 | 11/2003 | Vaisberg et al. | |
| 6,809,862 B2 | 10/2004 | Behnsen et al. | |
| 6,924,094 B1 | 8/2005 | Gingeras et al. | |
| 6,954,667 B2 | 10/2005 | Treado | |
| 7,286,222 B2 | 10/2007 | Gardner | |
| 7,616,320 B2 | 11/2009 | Javidi et al. | |
| 8,599,383 B2 | 12/2013 | Teitell | |
| 9,569,664 B2 | 2/2017 | Judkewitz | |
| 9,675,974 B2 | 6/2017 | Jooris et al. | |
| 9,684,281 B2 | 6/2017 | Mathuis et al. | |
| 2002/0064328 A1* | 5/2002 | Neuberger ............. A61B 18/22 385/1 |
| 2002/0106119 A1 | 8/2002 | Foran | |
| 2002/0164063 A1 | 11/2002 | Heckman | |
| 2003/0113832 A1 | 6/2003 | Lauf | |
| 2003/0199649 A1 | 10/2003 | Orbison et al. | |
| 2005/0036181 A1 | 2/2005 | Marquet et al. | |
| 2005/0272103 A1 | 12/2005 | Chen | |
| 2006/0014239 A1 | 1/2006 | Luttmann et al. | |
| 2006/0088814 A1 | 4/2006 | Hecht et al. | |
| 2006/0132799 A1 | 6/2006 | Franck et al. | |
| 2006/0283945 A1 | 12/2006 | Excoffier | |
| 2007/0216906 A1 | 9/2007 | Javidi et al. | |
| 2008/0018966 A1 | 1/2008 | Dubois et al. | |
| 2008/0032325 A1 | 2/2008 | DiMarzio | |
| 2008/0113340 A1 | 5/2008 | Schlegel | |
| 2008/0242556 A1 | 10/2008 | Cao et al. | |
| 2009/0082637 A1 | 3/2009 | Galperin | |
| 2009/0092227 A1 | 4/2009 | David | |
| 2009/0244667 A1 | 10/2009 | Frentz | |
| 2009/0296083 A1 | 12/2009 | Saski et al. | |
| 2009/0305393 A1 | 12/2009 | Joeris | |
| 2010/0034442 A1 | 2/2010 | Minakuchi | |
| 2010/0196871 A1 | 8/2010 | Dodgson | |
| 2010/0315501 A1 | 12/2010 | Ludwig | |
| 2011/0134426 A1 | 6/2011 | Kaduchak | |
| 2011/0204256 A1 | 8/2011 | Patt | |
| 2011/0212440 A1* | 9/2011 | Viovy ............... B01L 3/502761 435/6.1 |
| 2012/0015391 A1 | 1/2012 | Zhang et al. | |
| 2012/0200901 A1 | 8/2012 | Dubois | |
| 2012/0218379 A1 | 8/2012 | Ozcan | |
| 2014/0038171 A1 | 2/2014 | Metzger et al. | |
| 2014/0049634 A1 | 2/2014 | Tafas | |
| 2014/0193850 A1 | 7/2014 | Jooris et al. | |
| 2014/0195568 A1 | 7/2014 | Mathuis et al. | |
| 2014/0329231 A1 | 11/2014 | Magniette | |
| 2014/0349336 A1 | 11/2014 | Magniette | |
| 2015/0056607 A1 | 2/2015 | Jooris et al. | |
| 2017/0205222 A1 | 7/2017 | Mathuis et al. | |

FOREIGN PATENT DOCUMENTS

| | | |
|---|---|---|
| EP | 1524491 A1 | 4/2005 |
| EP | 2008715 A1 | 12/2008 |
| WO | WO 98/57152 | 12/1998 |
| WO | WO 99/44593 A1 | 9/1999 |
| WO | WO 2004/057464 A2 | 7/2004 |
| WO | WO 2004/102111 A1 | 11/2004 |
| WO | WO 2006/047252 A1 | 5/2006 |
| WO | WO 2007/073345 A1 | 6/2007 |
| WO | WO 2009/051741 A2 | 4/2009 |
| WO | WO 2009/151632 | 12/2009 |
| WO | WO 2009/154558 A1 | 12/2009 |
| WO | WO 2011/042442 A1 | 4/2011 |
| WO | WO 2011/068764 A2 | 6/2011 |
| WO | WO 2011/099925 A1 | 8/2011 |
| WO | WO 2011/154143 A1 | 12/2011 |
| WO | WO 2013/120886 A1 | 8/2013 |
| WO | WO 2014/044823 A1 | 3/2014 |

OTHER PUBLICATIONS

Beitsch et al., "Detection of carcinoma cells in the blood of breast cancer patients," The American Journal of Surgery, vol. 180, pp. 446-449 (Dec. 2000).

Boulet et al., "Cancer Epidemiology," Biomarkers & Prevention, 2008, 17(4): 810-817.

Daneshpanah et al., "3D Holographic Imaging and Trapping for Non-Invasive Cell Identification and Tracking," Journal of Display Technology, vol. 6(10), pp. 490-499 (Oct. 2010).

Extended European Search Report for European Patent Application No. 16151897.2, dated Jul. 21, 2016.0.

Frank Dubois et al. "Applications of digital holographic microscopes with partially spatial coherence sources", Journal of Physics: Conference Series, Institute of Physics Publishing, Bristol, GB, vol. 139, No. 1, p. 12027, XP020148183, ISSN: 1742-6596. Published Nov. 1, 2008.

Fu et al., "Quantitative DIC microscopy using an off-axis self-interference approach," Optics Letters, vol. 35(14), pp. 2370-2372 (Jul. 15, 2010).

Indebetouw, G. et al. Feb. 20, 2007. Scanning holographic microscopy with resolution exceeding the Rayleigh limit of the objective by superposition of off-axis holograms. Applied Optics 46(6): 993-1000. speif. pp. 993, 994.

Kemper, B. et al. Feb. 1, 2008. Digital holographic microscopy for live cell applications and technical inspection. Applied Optics 47(4): A52-A61. specif. pp. A52, 53, 56, 59.

Kemper et al., "Monitoring of laser micro manipulated optically trapped cells by digital holographic microscopy," J Biophoton, vol. 3(7), pp. 425-431 (2010).

Kemper et al., "Investigation of living pancreas tumor cells by digital holographic microscopy," Journal of Biomedical Optics, vol. 11(3), pp. 034005-1-034005-8 (May/Jun. 2006).

(56) References Cited

OTHER PUBLICATIONS

Kemper et al., "Simplified approach for quantitative digital holographic phase contrast imaging of living cells," Journal of Biomedical Optics, vol. 16(2), pp. 026014-1-026014-4 (Feb. 2011).

Kemper et al., "Self interference digital holographic microscopy approach for inspection of technical and biological phase specimens," Proceedings of the SPIE—The International Society for Optical Engineering SPIE—The International Society for Optical Engineering USA, vol. 8082, May 23, 2011.

Lee et al., "Incremental feature weight learning and its application to a shape-based query system," Pattern Recognition Letters, vol. 23, pp. 865-874 (2002).

Marin et al., "A meta-index for querying distributed moving object database servers," Information Systems, vol. 35, pp. 637-661 (2010).

McClatchey et al., "Object Databases in a Distributed Scientific Workflow Application," Information Technology, 1997, BIWIT '97., Proceedings of the Third Basque International Workshop on Biarritz, France, Jul. 2-4, 1997; Los Alamitos, CA, USA, IEEE Comput. Soc. US, Jul. 2, 1997, pp. 11-21.

Mihailescu M et al., "Microchannel-pinhole parameters investigation for cells visualization in holographic microscopy", Semiconductor Conference (CAS), 2011 International, IEEE pp. 75-78, XP032069149, DOI: 10.1109/SMICND.2011.6095718 ISBN: 978-1-61284-173-1. Published Oct. 17, 2011.

Moon et al., "Automated Three-Dimensional Identification and Tracking of Micro/Nanobiological Organisms by Computational Holographic Microscopy," Proceedings of the IEEE, vol. 97(6), pp. 990-1010 (Jun. 2009).

Nenadic et al., "A Possibility of Applying Differential Digital Holography in Manufacturing Process," 48th International Symposium ELMAR-2006, Jun. 7-9, 2006, Zadar, Croatia, pp. 103-106.

Owens et al., "Distinguishing Prostatic from Colorectal Adenocarcinoma on Biopsy Samples, The Role of Morphology and Immunohistochemistry," Arch Pathol Lab Med, vol. 131, pp. 599-603 (Apr. 2007).

Sahasranuddhe et al., Future Microbiol., 2011 6(9):1-25.

Sun et al., "Visualization of fast-moving cells in vivo using digital holographic video microscopy," Journal of Biomedical Optics, vol. 13(1), pp. 014007-1-014007-9 (Jan./Feb. 2008).

Reese et al., "Quantitative Analysis of Living Cells by Digital Holographic Microscopy," Biomedical Science & Engineering Conference, 2009, First Annual Ornl, IEEE, Piscataway, New Jersey, USA, pp. 1-4 (Mar. 18, 2009).

Weigum et al., "Nano-Bio-Chip Sensor Platform for Examination of Oral Exfoliative Cytology," Cancer Prevention Research, vol. 3, pp. 518-528 (2010).

White et al., "Isolation of Stool-Derived Mucus Provides a High Yield of Colonocytes Suitable for Early Detection of Colorectal Carcinoma," Cancer Epidemiol Biomarkers Prev, vol. 8, pp. 2006-2013 (2009).

Yong-Seok Choi et al., "Lateral and cross-lateral focusing of spherical particles in a square microchannel", Lab on a Chip, vol. 11, No. 3, pp. 460-465, XP55032064, ISSN: 1473-0197, DOI: 10.1039/cOIc00212g. Published Feb. 1, 2011.

Zhou et al., "An Image Clustering and Retrieval Framework Using Feedback-based Integrated Region Matching," 2009 International Conference on Machine Learning and Applications, 2009, ICMLA '09, IEEE, Piscataway, New Jersey, USA, Dec. 13, 2009, pp. 596-601.

International Search Report for Application No. PCT/EP2014/066312, dated Jan. 10, 2014, in 3 pages.

\* cited by examiner

DIGITAL HOLOGRAPHIC MICROSCOPE WITH FLUID SYSTEMS

CROSS-REFERENCE TO RELATED APPLICATIONS

This application is the U.S. National Phase under 35 U.S.C. § 371 of International Application PCT/EP2013/069625, filed Sep. 20, 2013, which claims priority to EP 12185229.7, filed Sep. 20, 2012.

TECHNICAL FIELD

The invention pertains to the technical field of analyzing and monitoring the state and the processes in a reactor or incubator, using a digital holographic microscope (DHM). More in particular, the reactor may contain a fluid medium, and can be e.g. a bio-reactor containing biological organisms such as cells, bacteria, yeasts, micro-organisms, nematodes or any combination thereof in a liquid medium.

BACKGROUND

In biology, biotechnology, chemistry and related areas such as bio-chemistry, yeasting factories, breweries, . . . , practical use is made of reactors, containers or incubators comprising a fluid medium, or samples which contain a fluid medium, into which certain processes occur, whereby the environmental parameters are under control. Examples are cell diagnostics and research laboratories where cell processes are to be monitored or observed, breweries such as beer breweries, where yeasting processes may have to be closely monitored, etc. Other examples are fermentators or fermentation reactors, water supply systems, plumbing, sewer systems, water canalizations, water quality improving and/or inspection installations or water purification plants, etc. where the objects in suspension are to be monitored or analyzed. To analyze and/or monitor the state and/or processes in the reactor, one has a choice between bringing the analysis apparatus to the reactor or taking samples from the reactor to the analysis apparatus. In the former case, typical problems are e.g. that the analysis apparatus needs to be resistant to the specific environment in the reactor, that the apparatus, when reused with another reactor, does not contaminate this other reactor, that the analysis apparatus is very expensive, that the apparatus is not accurate enough, etc.; in the latter case, a typical problem is the often time-consuming and/or labor-intensive gathering and preparing of samples for further observation or analysis. In such cases, it may be impossible to accurately monitor the state and/or processes of the reactor, as the time delay between the gathering of a sample and the analysis results may become too big.

Patent application US 2010/0315501 A1 discloses an electronic imaging flow-microscope for remote environmental sensing, bioreactor process monitoring, and optical microscopic tomography applications. Hereby, a fluid conduit has a port on each end of a thin flat transparent fluid transport region. A planar illumination surface contacts one flat side of the transparent fluid transport region and a planar image sensing surface contacts the other flat side. Light from the illumination surface travels through the transparent fluid transport region to the planar image sensing surface, producing a light field affected by the fluid and objects present. The planar image sensing surface creates electrical image signals responsive to the light field. The planar illumination surface can be light emitting elements such as LEDs, OLEDs, or OLET, whose illumination can be sequenced in an image formation process. The flow microscope can further comprise flow-restricting valves, pumps, energy harvesting arrangements, and power management.

However, traditional flow microscopes do not always provide enough information on the objects suspended in a flow. In some applications, three-dimensional data is to be acquired from these objects. Therefore, digital holographic imaging techniques may be applied.

Holography is a three-dimensional (3D) imaging technique that makes use of the interference between a reference wave and a wave emanating from the sample called object wave. The purpose of this interference is to record the phase of the object wave, which is related to the 3D character of the sample. With digital holographic imaging (DHI), real-time observations can be achieved by using a charged coupled device (CCD) camera as recording device and by performing a numerical reconstruction of the hologram. This idea has been proposed for the first time over 30 years ago by J. W. Goodmann, R. W. Lawrence, in "Digital image formation from electronically detected holograms," Appl. Phys. Lett, Vol. 11, 1967. As a result of technological progresses achieved in the fields of digital image acquisition and processing, this numerical or digital approach of holography has considerably extended the fields of its potential applications and different types of DHI-inspired imaging systems have been developed during the last years.

DHI techniques can be classified in two main categories: in-line techniques characterized by the fact that the reference and object waves have similar propagation directions, and off-axis techniques for which the two interfering waves propagates along different direction. The procedure for hologram formation in in-line digital holography is similar to the procedure used for phase measurements with so-called phase-shifting interferometric techniques. Hologram formation with in-line techniques requires the acquisition of several images, at least three, that must be recorded during a modulation of the reference phase. Off-axis techniques, are more simple from the experimental point of view since they require a single hologram acquisition without modulation of the phase of the reference wave. In-line techniques however present the advantage that the reconstructed images are free of twin images and zero order of diffraction. Among off-axis techniques, we can distinguish methods based on Fourier-transform holography, and methods based on a so-called Fresnel holography. With Fourier-transform methods the reference wave must be a spherical wave of precisely controlled curvature and image reconstruction is basically performed by Fourier transformation of the hologram. With Fresnel-holography based techniques, the reconstruction procedure is more sophisticated but more flexibility is offered to build experimental installations.

Among recent publications presenting developments or applications of DHI-inspired techniques, we can mention the following works. A study of some general performances of an in-line technique is presented in "Image formation in phase-shifting digital holography and application to microscopy", 1. Yamaguchi et al., Applied Optics, Vol. 40, No. 34, 2001, pp. 6177-6186. In "Fourier-transform holographic microscope", Applied Optics, Vol. 31, 1992, pp. 4973-4978, W. S. Haddad et al describe the general principle of Fourier-transform DHI.

Examples of applications of the Fresnel-based approach can be found in "Direct recording of holograms by a CCD target and numerical reconstruction", U. Schnars and W. Juptner, Applied Optics, Vol. 33, 1994, pp. 179-181, and in "Performances of endoscopic holography with a multicore optical fiber", O. Coquoz et al., Applied Optics, Vol. 34, 1995, pp. 7186-7193.

A key element of a DHI method is the numerical method used for hologram reconstruction. An original reconstruction procedure, which allows for reconstructing simultaneously the amplitude and the phase of the object wave, on the basis of a single off-axis hologram acquisition, has been developed by Cuche et al. and is presented in U.S. Pat. No. 6,262,218, and in WO 00/20929. Different applications and implementations of this technique are presented in "Digital holography for quantitative phase-contrast imaging", Optics Letters, Vol. 24, 1999, pp. 291-293, in "Simultaneous amplitude-contrast and quantitative phase-contrast microscopy by numerical reconstruction of Fresnel off-axis holograms", Applied Optics, Vol. 38, 1999, pp. 6994-7001, in "Spatial Filtering for Zero-Order and Twin-Image Elimination in Digital Off-Axis Holography", Applied Optics, Vol. 38 No. 34, 1999, in "Aperture apodization using cubic spline interpolation: Application in digital holographic microscopy", Optics Communications, Vol. 182, 2000, pp. 59-69, and in "Polarization Imaging by Use of Digital Holography", T. Colomb et al., Applied Optics, Vol. 38, No 34, 1999.

DHI method presents interesting possibilities of applications in cell biology. Indeed a living cell behaves optically as a phase object, i.e. a transparent sample whose constituents can be optically probed on the basis of the phase shift they induce on the light crossing them.

The phase-shifting behavior of transparent sample is well known, and for a long time as it constitutes the mechanism of image formation in phase-contrast (PhC) and Nomarski (DIC) microscopy. Even though these two techniques are widely used in biological microscopy, and well suited as contrasting methods, they cannot be used for precise quantitative phase measurements. The DHI method instead, is reminiscent of classical interferometry, which is the most commonly used technique for phase measurements. However, whereas interferometric techniques are widely used in metrology, only few biological applications have been reported, by R. Barer and S. Joseph, in "Refractometry of living cells", Quarterly Journal of Microscopical Science, Vol. 95, 1954, pp. 399-423, by R. Barer in "Refractometry and interferometry of living cells", Journal of the Optical Society of America, Vol. 47, 1957, pp. 545-556, by A. J. Coble et al. in "Microscope interferometry of necturus gallblader epithelium", Josiah Macy Jr. Fundation, New York, 1982, p. 270-303, by K. C. Svoboda et al. in "Direct observation of kinesin stepping by optical trapping interferometry", Nature, Vol. 365, 1993, by J. Farinas and A. S. Verkman, in "Cell volume plasma membrane osmotic water permeability in epithelial cell layers measured by interferometry", Biophysical Journal, Vol. 71, 1996, pp. 3511-3522, by G. A. Dunn and D. Zicha in "Dynamics of fibroblast spreading", Journal of Cell Science, Vol. 108, 1995, pp. 1239-1249.

For biological applications, as well as for material science or metrology applications, DHI methods offer a novel alternative to classical interferometry with similar performances but simplified experimental procedures. The main advantage originates from the fact that complex and costly experimental optical devices can be handled by digital processing methods. For example, as described by E. Cuche et al. in "Simultaneous amplitude-contrast and quantitative phase-contrast microscopy by numerical reconstruction of Fresnel off-axis holograms", Applied Optics, Vol. 38, 1999, pp. 6994-7001, the wave front deformations appearing when a microscope objective is introduced along the path of the object wave can be compensated using a digital procedure. This particular feature opens attractive possibilities in the fields of microscopy. In addition DHI techniques performs faster than interferometric techniques, and provides more information about the sample, in particular, the amplitude and the phase of the object wave can be obtained simultaneously on the basis of a single hologram acquisition.

DHI methods have been applied to static imaging of biological cells, without phase reconstruction by K. Boyer et al. in "Biomedical three-dimensional holographic microimaging at visible, ultraviolet and X-ray wavelength", Nature Medicine, Vol. 2, 1996, pp. 939-941, and by F. Dubois et al. in "Improved three-dimensional imaging with a digital holography microscope with a source of partial spatial coherence", Applied Optics, Vol. 38, 1999, pp. 7085-7094. DHI of cells using a phase measurement modality requiring several image acquisitions has been reported by G. Indebetouw and P. Klysubun in "Saptiotemporal digital microholography", Journal of the Optical Society of America A, Vol. 18, 2001, pp. 319-325.

With DHI, image acquisition can be performed at video-rate, and even faster using appropriate image acquisition systems, for experimental periods of up to several hours. Due to its interferometric nature, DHI has a high axial resolution (nanometer scale), which allows for observing subtle and minute modifications of sample shape, opening a wide field of applications in both life and material sciences. With the event of video-rate image acquisition by DHI, it has become possible to use DHI with a flow microscope, even at high flow rates.

WO2003048868 discloses an apparatus and a method for performing digital holographic imaging of a sample which includes a holographic creation unit, a holographic reconstruction unit, a processing unit, and a sample unit. The sample unit includes a container that contains a medium in which a sample is located.

U.S. Pat. No. 7,463,366 discloses a method and device for obtaining a sample with three-dimensional microscopy, in particular a thick biological sample and the fluorescence field emitted by the sample. One embodiment includes obtaining interferometric signals of a specimen, obtaining fluorescence signals emanating from the specimen, recording these signals, and processing these signals so as to reconstruct three-dimensional images of the specimen and of the field of fluorescence emitted by the specimen at a given time. Another embodiment includes a digital holography microscope, a fluorescence excitation source illuminating a specimen, where the microscope and the fluorescence excitation source cooperate to obtain interferometric signals of the specimen and obtain fluorescence signals emanating from the specimen, means for recording the interferometric signals and fluorescence signals, and means for processing the interferometric signals and the fluorescence signals so as to reconstruct three-dimensional images of the specimen and of the field of fluorescence emitted by the specimen at a given time.

Patent application WO2004102111 discloses a compact microscope able to work in digital holography for obtaining high quality 3D images of samples, including fluorescent samples and relatively thick samples such as biological samples, said microscope comprising illumination means at least partially spatially coherent for illuminating a sample to be studied and a differential interferometer for generating interfering beams from said sample on the sensor of an electronic imaging device, said interferometer comprising namely tilting means for tilting by a defined angle one the interfering beams relatively to the other, said tilting resulting into a defined shift of said interfering beam on the sensor of the electronic imaging device, said shift being smaller than spatial coherence width of each beam, said microscope being able to be quasi totally preadjusted independently from the samples so that minimum additional adjustments are required for obtaining reliable 3D images of samples.

However, the above mentioned prior art DHI techniques do not disclose how one can obtain data from an extensive sample of objects suspended in a fluid, nor the possibility of obtaining such data within a relatively short period. More in particular, most prior art DHI techniques focus on the imaging of small samples contained within a small specimen, whereby the accuracy and 3D imaging of DHI is being exploited, rather than its high rate of obtaining 3D information.

The problems in the prior art are multiple. The data acquired with the analysis apparatus of the prior may not be accurate enough, it may not be obtained quickly enough, the apparatus may be too expensive, it may only give two-dimensional and/or analogue images whereby three-dimensional information is obtained only after e.g. making a set of 2D images, digitalization and performing a CT-processing step. More in particular, DHMs may provide images and/or directly digitalized information about samples which is superior to other imaging or analysis techniques, but can be rather expensive. Furthermore, the gathered sample may need to be processed before analysis, which can be a time-consuming and labor-intensive procedure. Contamination may be an issue when the same apparatus is used to monitor or analyze different reactors, or the same reactor at different positions of times. Prior art techniques may not always provide the possibility of returning the sample to the reactor or to another reactor, or the possibility of real-time monitoring and providing timely feedback for adapting the reactor's environmental parameters.

There remains a need in the art for an improved system for the monitoring and/or analysis of one or more reactors and/or incubators comprising a fluid medium or comprising sample containing a fluid medium, in particular biological or biochemical cultures of organisms such as cells, bacteria, yeasts, micro-organisms, nematodes or any combination thereof, preferably in a liquid.

The present invention aims to resolve at least some of the problems mentioned above.

The invention thereto aims to provide an improved system for the monitoring and/or analysis of one or more reactors and/or incubators comprising a digital holographic microscope (DHM) and one or more fluidic systems which are capable of guiding a sample of the contents of a reactor with a fluid medium to the DHM for analysis and preferably back to the reactor. As such, one DHM can serve to analyze or monitor multiple reactors, and/or one reactor at different positions, e.g. at different heights, or at different times. The fluidic systems may be arranged such that contamination is avoided and replacement is easy.

SUMMARY OF THE INVENTION

The present invention provides but is not limited to a fluid microscope system for analyzing and/or monitoring the contents of one or more fluid-based reactors, comprising:
   a digital holographic microscope (DHM) capable of obtaining phase information of a fluid sample and comprising illumination means;
   one or more fluidic systems connected to said reactors and to said DHM, capable of guiding fluid from said reactors to said DHM, whereby preferably at least one fluidic system comprises one or more tubes which may come in direct contact with fluid from said reactor;
characterized in that preferably at least one tube comprises a part which is at least partially transparent for the illumination means of said DHM for obtaining holographic information of said fluid sample.

In a preferred embodiment, the present invention provides a fluid microscope system as described above, whereby said tube comprises a part which is at least partially transparent for the illumination means of said DHM and which has a shape suitable for said DHM.

In a preferred embodiment, the present invention provides a fluid microscope system as described above, whereby said tube has a shape comprising two parallel transparent sides and whereby said DHM is capable of working in transmission mode.

In a preferred embodiment, the present invention provides a fluid microscope system as described above, whereby said tube comprises a flow cell and/or a microfluidic system.

In a preferred embodiment, the present invention provides a fluid microscope system as described above, whereby said tube comprises at least one transparent side and whereby said DHM is capable of working in reflection mode.

In a preferred embodiment, the present invention provides a fluid microscope system as described above, comprising at least one pumping system connected to said one or more fluidic systems and capable of inducing a fluid flow in said fluidic systems.

In a preferred embodiment, the present invention provides a fluid microscope system as described above, whereby at least one fluidic system forms a closed circuit between one of said reactor and said DHM and back to said reactor.

In a preferred embodiment, the present invention provides a fluid microscope system as described above, whereby at least one fluidic system comprises a reactor attachment system for easily attaching and/or detaching said fluidic system to said reactor, whereby leakage of fluid is prevented.

In a preferred embodiment, the present invention provides a fluid microscope system as described above, whereby at least one fluidic system comprises a fluid-tight flexible part which, when compressed, pulled and/or pushed results in a fluid flow in said fluidic system.

In a preferred embodiment, the present invention provides a fluid microscope system as described above, comprising a pumping system with a pump connected to said fluidic system, capable of compressing, pulling and/or pushing said fluid-tight flexible part, thereby inducing a fluid flow in said fluidic system.

In a preferred embodiment, the present invention provides a fluid microscope system as described above, whereby at least one pumping system comprises a stepwise pump, capable of inducing a stepwise fluid flow in a fluidic system to which said stepwise pump is connected.

In a preferred embodiment, the present invention provides a fluid microscope system as described above, whereby at least one pumping system comprises a continuous pump, capable of inducing a continuous fluid flow in a fluidic system to which said continuous pump is connected. In a more preferred embodiment, said pump is a peristaltic pump.

In a further aspect, the present invention provides a tube for a fluidic system of a fluid microscope system as described above, comprising a part which is at least partially transparent for illumination means of a DHM of said fluid microscope system.

In a preferred embodiment, the present invention provides a tube as described above, whereby said part comprises two parallel transparent sides.

In a preferred embodiment, the present invention provides a tube as described above, whereby said tube is autoclavable.

In a preferred embodiment, the present invention provides a tube as described above, whereby said part comprises a flow cell and/or a microfluidic system.

In a further aspect, the present invention provides a package system comprising a tube as described above, and a package for protecting said tube.

In a preferred embodiment, the present invention provides a package system as described above, whereby said package encloses said tube, thereby protecting said tube against external contamination.

In a preferred embodiment, the present invention provides a package system as described above, whereby said tube is sterile.

In yet a further aspect, the present invention provides a fluidic system for a fluid microscope system as described above, comprising one or more tubes comprising a part which is at least partially transparent for illumination means of a DHM of said fluid microscope system.

DETAILED DESCRIPTION OF THE INVENTION

Figure 1:
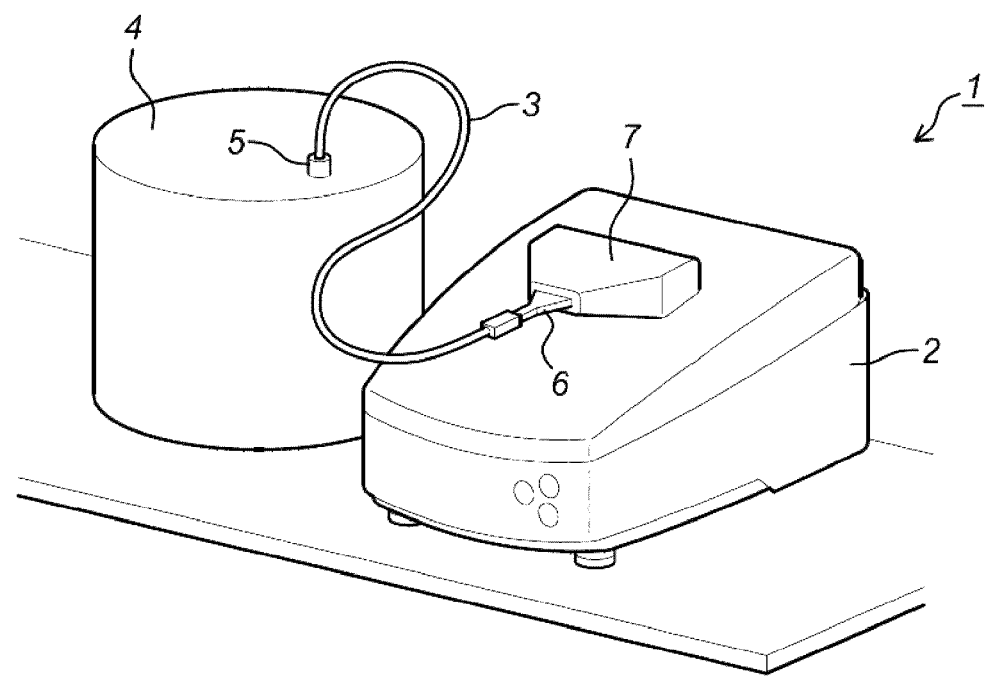
FIG. 1 illustrates a setup whereby a fluid microscope system is connected to one reactor, such as a bio-reactor.

The present invention concerns a system for analyzing and/or monitoring the contents of one or more fluid-based reactors.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

The term "reactor" as used herein refers to a container or a canalization system capable of holding and/or guiding a fluid wherein objects or processes of interest are present. As such, the terms "reactor", "incubator", "container", "bioreactor", etc. are assumed to be synonyms unless the context dictates otherwise. Examples of reactors can be fermentation reactors, water supply piping or plumbing, water canalization systems, water purification reactors, brewing reactors, micro-reactors, etc.

The expression "online monitoring of a reactor", here and throughout the description unless otherwise defined, refers to monitoring when the reactor is online, i.e. when reactions are taking place or should be taking place in the reactor.

The expression "inline monitoring of a reactor", here and throughout the description unless otherwise defined, refers to monitoring inside a circuit, i.e. the content which is to be monitored is following a circuit and the monitoring occurs at a certain position in this circuit.

The expression "in situ monitoring of a reactor", here and throughout the description unless otherwise defined, refers to monitoring inside the reactor.

The expression "real-time monitoring of a reactor", here and throughout the description unless otherwise defined, refers to the monitoring of processes in the reactor at time intervals which are smaller than or of the same magnitude as the typical time of the monitored processes or inversely proportional to the process rate. This may allow for a monitoring of different stages of a process or of different stages of the content of the reactor in time; furthermore, this may allow for actions to be taken directly or almost directly after a specific process or stage has been observed in the reactor.

The term "fluid" as used herein refers to the known state of matter which continually deforms or flows under an applied shear stress. In practice, fluids are liquids, gasses or vapours, a combination of one or more liquids and/or gasses, all of which may contain objects such as solid particles, organisms such as cells, bacteria, yeasts, micro-organisms, nematodes or any combination thereof, contamination, etc. in solution, suspension or other type of mixture. Preferably, in the present invention disclosure, a fluid is in the liquid state, such as a liquid, a liquid mixture, a solution, a suspension, an emulsion, etc.

In a first aspect, the invention provides a system for analyzing and/or monitoring the contents of one or more fluid-based reactors, comprising:
- a digital holographic microscope (DHM) capable of obtaining phase information of a fluid sample and comprising illumination means;
- one or more fluidic systems connected to said reactors and to said DHM, capable of guiding fluid from said reactors to said DHM, whereby preferably at least one fluidic system comprises one or more tubes which may come in direct contact with fluid from said reactor;

whereby preferably at least one tube comprises a part which is at least partially transparent for the illumination means of said DHM for obtaining phase information of said fluid sample.

Other microscopic techniques then digital holographic microscopy may not be fast or accurate enough for the monitoring of the processes in the reactor and circuit system. Such other microscopic techniques may not be applied 'inline', but need to take a sample, possibly apply a die or coloring, apply the sample to a slide, and use a microscope to observe the sample on the slide. This process is time consuming and labor intensive, and therefore not suitable for automation. Other microscope techniques may give analogue images, which then may be stored digitally e.g. through an additional scanning step. With DHM, the information is digitally obtained and can be processed digitally directly, i.e. one does not need an extra digitalization procedure. Furthermore, a DHM does not lead to the loss of the sample, as the sample can be returned to the reactor if desired. Other microscopic techniques may not have that advantage, due to the use of e.g. coloring, slides, adding necessary markers, etc.

Using a DHM for analyzing and/or monitoring the state of and reactions in a reactor offers many advantages as compared to other analyzing/monitoring techniques, such as
- the possibility of inline 3D/4D monitoring instead of the work-intensive method of collecting or hand-collecting samples at specific moments and from specific reactors and subsequent analysis on (2D/3D) microscopic systems such as traditional microscopes, phase contrast microscopes or confocal microscopes;
- the greater amount of information about a sample gathered in a shorter period of time compared to other microscopic techniques;
- the possibility of automated digitalization and even automated qualification and quantification of the sample, etc.

DHM offers directly digitalized phase information which allows 3D imaging. This is faster than other 3D imaging techniques such as CT scans which first obtain a large set of 2D images from which a 3D image is reconstructed, possibly after an extra digitalization step. Therefore, the present invention leads to a faster, more accurate and more reliable analyzing and/or monitoring of reactors by using DHM as an observation, analysis and/or monitoring apparatus or mechanism. DHM is also more apt than other microscopy system for analyzing fluid, more preferably liquid, samples, especially for obtaining 3D information, because it is faster and more accurate than e.g. CT techniques.

Digital Holographic Microscopy (DHM) is a technique which allows a recording of a 3D sample or object without the need of scanning the sample layer-by-layer. In this respect DHM is a superior technique to confocal microscopy. In DHM, a holographic representation is recorded by a digital camera such as a CCD- or a CMOS-camera, which can subsequently be stored or processed on a computer.

To make a holographic representation, or hologram, traditionally a highly coherent light source such as laser-light, is used to illuminate the sample. In the most basic set-up, the light form the source is split into two beams, an object beam and a reference beam. The object beam is sent via an optical system to the sample and interacts with it, thereby altering the phase and amplitude of the light depending on the object's optical properties and 3D shape. The object beam which has been reflected on or transmitted through the sample, is then made (e.g. by set of mirrors and/or beam splitters) to interfere with the reference beam, resulting in an interference pattern which is digitally recorded. Since the hologram is more accurate when object beam and reference beam have comparable amplitude, an absorptive element can be introduced in the reference beam which decreases its amplitude to the level of the object beam, but does not alter the phase of the reference beam or at most changes the phase globally, i.e. not dependent on where and how the reference beam passes through the absorptive element. The recorded interference pattern contains information on the phase and amplitude changes which depend on the object's optical properties and 3D shape.

An alternative way of making a hologram is by using the in-line holographic technique. In-line DHM is similar to the more traditional DHM, but does not split the beam, at least not by a beam splitter or other external optical element. In-line DHM is most preferably used to look at a not-too-dense solution of particles, e.g. cells, in a fluid. Thereby some part of the at least partially coherent light will pass through the sample without interacting with the particles (reference beam) and interfere with light that has interacted with the particles (object beam), giving rise to an interference pattern which is recorded digitally and processed. In-line DHM is used in transmission mode, it needs light with a relatively large coherence length, and cannot be used if the samples are too thick or dense.

Another DHM technique called differential DHM (DDHM) is disclosed in European patent EP 1 631 788. DDHM is different to the other techniques in that it does not really make use of reference and object beams. In a preferred set-up of DDHM, the sample is illuminated by illumination means which consist of at least partially coherent light in reflection or in transmission mode. The reflected or transmitted sample beam can be sent through an objective lens and subsequently split in two by a beam splitter and sent along different paths in a differential interferometer, e.g. of the Michelson or Mach-Zehnder type. In one of the paths, a beam-bending element or tilting means is inserted, e.g. a transparent wedge. The two beams are then made to interfere with each other in the focal plane of a focusing lens and the interference pattern in this focal plane is recorded digitally and stored by e.g. a CCD-camera connected to a computer. Hereby, due to the beam-bending element, the two beams are slightly shifted in a controlled way and the interference pattern depends on the amount of shifting. Then the beam-bending element is turned, thereby altering the amount of shifting. The new interference pattern is also recorded. This can be done a number N of times, and from these N interference patterns, the gradient (or spatial derivative) of the phase in the focal plane of the focusing lens can be approximately computed. This is called the phase-stepping method, but other methods of obtaining the phase gradient are also known, such as a Fourier transform data processing technique. The gradient of the phase can be integrated to give the phase as a function of position. The amplitude of the light as a function of position can be computed from the possibly but not necessarily weighted average of the amplitudes of the N recorded interference patterns. Since phase and amplitude are thus known, the same information is obtained as in a direct holographic method (using a reference and an object beam), and a subsequent 3D reconstruction of the object can be performed.

The use of DHM in a diagnostic setting has many advantages which makes it the ideal technique to implement in a setting such as in the current invention. Besides a bright field image, a phase shift image is created as well. The phase shift image is unique for DHM and gives quantifiable information about optical distance. In reflection DHM, the phase shift image forms a topography image of the object.

Transparent objects, like living biological organisms such as cells, bacteria, yeasts, micro-organisms, nematodes or any combination thereof, are traditionally viewed in a phase contrast microscope or in a differential interference contrast microscope. These methods visualize phase shifting transparent objects by distorting the bright field image with phase shift information. Instead of distorting the bright field image, transmission DHM creates a separate phase shift image showing the optical thickness of the object. This can also be achieved with a DHM working in reflection mode for both transparent as opaque objects. Digital holographic microscopy thus makes it possible to visualize and quantify transparent and/or opaque objects and is therefore also referred to as quantitative phase contrast microscopy. More so, DHM allows imaging subcellular structures in three dimensions.

An object image is calculated at a given focal distance. However, as the recorded hologram contains all the necessary object wave front information, it is possible to calculate the object at any focal plane by changing the focal distance parameter in the reconstruction algorithm. In fact, the hologram contains all the information needed to calculate a complete image stack. In a DHM system, where the object wave front is recorded from multiple angles, it is possible to fully characterize the optical characteristics of the object and create tomography images of the object.

Furthermore, as DHM systems do not have an image forming lens, traditional optical aberrations do not apply to DHM. Optical aberrations are "corrected" by design of the reconstruction algorithm. A reconstruction algorithm that truly models the optical setup will not suffer from optical aberrations. In optical microscopy systems, optical aberrations are traditionally corrected by combining lenses into a complex and costly image forming microscope objective. Furthermore, the narrow focal depth at high magnifications requires precision mechanics. Lastly, the needed components for a DHM system are inexpensive optics and semiconductor components, such as a laser diode and an image sensor. The low component cost in combination with the auto focusing capabilities of DHM, make it possible to manufacture DHM systems for a very low cost. Nevertheless, the cost of a DHM may still be too high for monitoring a large amount of reactors. For this, the present invention provides a system comprising one DHM and a set of fluidic circuits which are capable of guiding fluid samples from multiple reactors to the DHM and preferably back. Hereby, only one DHM is needed to monitor multiple reactors and the overall cost can be reduced.

Generally, a DHM comprises illumination means which comprises a coherent light source or an at least partially coherent light source such as a LASER or LED, an interferometer which may comprise a set of mirrors and/or beam splitters, and digital recording means such as a CCD or CMOS camera and e.g. a flash card or magnetic recording device connected to it for long-time storage. A DHM may also comprise further optical components such as lenses, mirrors, prisms, attenuators, etc. Possibly, a DHM may comprise or may be connected to processing means such as a mainframe, a PC, a logical device such as a PLC, etc. A DHM may work in transmission and/or reflection mode, preferably depending on the nature of the sample which is to be observed. A DHM as used in the system of the present invention may be a traditional DHM, an in-line DHM, a differential DHM, or another kind of DHM.

However, DHM may be expensive to use for inline, in-situ, online and/or real-time analyzing and/or monitoring of the state and processes in reactors. In a laboratory with many reactors, it would be expensive to have one DHM per reactor for monitoring and analysis. The present invention solves this problem by providing one or more fluidic systems which may connect the contents of the reactor to a central DHM-unit. Thereby, one DHM may be used in combination with different reactors or with one reactor whereby information about the reaction process and state is required at different positions in the reactor or at different times.

In an embodiment, at least one fluidic system comprises one or more tubes which may come in direct contact with fluid from said reactor. Preferably said tubes comprise a bendable material which is still resistant against possible kinks. The advantage of using tubes in the fluidic system for guiding the fluid is that they can be produced cheaply and can be made long enough for the application at hand, or can be combined to a long fluid-guiding channel. In a more preferred embodiment, only the tubes, more preferably easily replaceable tubes, may come in direct contact with the fluid of the reactor. Thereby, other components of the fluidic system can be reused without the necessity of, possibly expensive, cleaning or decontamination procedures.

In a preferred embodiment, at least one tube comprises a part which is at least partially transparent for the illumination means of said DHM for obtaining phase information of said fluid sample. In this case, the tube can be lead to the DHM for direct analysis of its contents, i.e. there is no need for an extra component, which could lead to a more expensive system, or to leaks in the fluidic system due to bad or wrong connections between a tube and the extra component.

For inline monitoring and/or analyzing of a reactor with a DHM, optical contact is needed between DHM and at least a sample of the reactor's content, preferably without the need to remove that sample from the reactor completely, hence 'inline'. Therefore, one or more tubes of the fluidic systems may comprise at least a part which provides optical contact with the DHM, preferably the properties of said part are optimized to the specifications of the DHM. Furthermore, in a preferred embodiment, the fluidic system comprises one or more tubes for guiding a sample of the contents of the reactor to the DHM and back to the reactor and/or to another reactor. In such an embodiment, the fluidic system leads fluid from one reactor to the DHM and then either back to the same reactor, or to another, possibly depending on the images obtained by the DHM, or to the same reactor but at a different position/height, etc. Since the DHM is able to acquire information about the sample fast and accurately, it can use this information in real-time to decide what needs to be done with the content of the observed sample. Thereto, in a preferred embodiment, the fluidic system may comprise one or more, preferably electronically steered, valves and a decision-making unit which is operably connected to the valves and the DHM and which decides on which valves to open and/or close at which time, depending on the information required by the DHM.

To avoid contamination of the sample taken from one reactor e.g. by remains from another reactor, the parts of the fluidic system circuits which may come into direct contact with fluids from reactors, should be easily replaceable. In this way, the parts that do not come into contact with fluid from reactors, can be re-used. This has many advantages: the replaceable parts may at least partly be made from cheap materials, only the part which should provide optimal optical contact with the DHM may need to be expensive, the re-usable parts may be more expensive and of better quality as they will need to last a longer time. If the re-usable parts are cheap to manufacture, this is also fine. More in particular, the manufacturer of the system of the present invention has a choice in how to make the re-usable parts which can be optimized according to the specific use of the system. Replaceable parts of the system do not need to be decontaminated or sterilized, hereby gaining time and saving costs, but can be produced in large quantities, leading to reduced costs. Therefore, in a preferred embodiment, the fluidic system comprises tubes which are easily replaceable and/or cheap to manufacture.

The terms "sample" and "fluid sample" as used herein is to be understood as a sample of the contents of a reactor containing specimens in a fluid state. Preferably, the fluid state is a liquid state and the sample is a liquid sample. Samples may be any specimen obtained from a chemical reaction, such as a catalytic reaction, a soil specimen, a specimen comprising micro-organisms and/or insects, a forensic specimen or a specimen from a crime scene, such as, but not limited to a hair specimen, body fluids, a water specimen, an entomological specimen, a biological specimen comprising organisms such as cells, bacteria, yeasts, micro-organisms, nematodes or any combination thereof, etc., which may be put into a fluid state if necessary, e.g. by dissolving, by suspending, by mixing, . . . .

A system as disclosed in this text is suited to monitor multiple reactors or at least multiple samples, using a limited set of DHMs. In a preferred embodiment, the DHM of the present invention comprises a multiple-sample scanning system for observing or scanning multiple samples using the same DHM. This multiple-sample scanning system may comprise a scanning stage, which preferably is motorized, capable of moving multiple samples subsequently in the optical path of the illumination means of the DHM, and/or this multiple-sample scanning system may comprise an optical guiding system capable of changing the optical path of the illumination means of the DHM such that the multiple samples are subsequently placed in the illumination beam of the illumination means. Such an optical guiding system may comprise one or more mirrors, which may be or become partially transparent, optical fibers, liquid crystal devices, lenses, parabolic mirrors, etc. all of which may be motorized and, preferably, electromechanically and/or electronically steered. Therefore, in a preferred embodiment, the multiple-sample scanning system is operably connected to the DHM.

In a preferred embodiment, the system of the present invention comprises a central unit connected to the DHM or part of the DHM, which is capable of adjusting the DHM, in particular the working parameters of the DHM. In a more preferred embodiment, the system comprises a multiple-sample scanning system, operably connected to said central unit, whereby the central unit is capable of steering said multiple-sample scanning system, thereby subsequently selecting multiple samples for observation by said DHM.

In a preferred embodiment, the DHM comprises a multiple-sample scanning system for easily changing the position of the multiple samples or the path of the illumination beam of the illumination means of the DHM in order to stepwise observe multiple samples contained in different fluidic systems/tubes. This system may comprise a set of optical components, such as mirrors, optical fibers, partially reflecting, opaque and/or transparent surfaces, prisms, lenses, beam splitters, etc., all of which may be electromechanically or electronically steered to reflect and/or transmit light into specific directions.

In a preferred embodiment, said tube comprises a part which is at least partially transparent for the illumination means of said DHM and which has a shape suitable for said DHM, preferably a slab-like shape. In a more preferred embodiment, said DHM is capable of working in transmission mode and said tube has a shape comprising two parallel sides, transparent for the illumination means of said DHM. In another more preferred embodiment, said DHM is capable of working in reflection mode and said tube comprises at least one, preferably flat, side which is transparent for the illumination means of said DHM.

In a preferred embodiment, said tube comprises a part which is at least partially transparent for the illumination means of said DHM and which comprises a flow cell and/or a microfluidic system. In a more preferred embodiment, said flow cell and/or microfluidic system comprises a cross section in which the height and/or width varies along the cross section. This allows obtaining clear holographic images for a variety of concentrations of objects suspended in the fluid. A high concentration of suspended objects could lead to a large number of objects being stacked on top of one another and may lead to difficulties in obtaining a holographic image, especially if the DHM works in transmission mode. A low concentration could result in the DHM obtaining holographic images of the fluid medium only and not of an object suspended in that medium. If the concentration is high, a holographic image can be obtained at the position where the height or width is small, thereby ensuring that not too many objects are stacked in the illumination beam. If the concentration is small, a holographic image can be obtained at the position where the height or width is large, thereby ensuring that at least one suspended object is in the illumination beam. In a more preferred embodiment, said microfluidic system comprises a branching of said tube in multiple tubes of preferably different cross sections, diameters, heights and/or widths. Such an arrangement also allows obtaining clear holographic images for a variety of concentrations of objects suspended in the fluid. Preferably, the cross section, diameter, height and/or width of said flow cell and/or microfluidic system is chosen in function of the size of the suspended objects and/or the size of the illumination beam of the DHM. More preferably, the narrowest dimension in a cross section of said flow cell and/or microfluidic system is larger than 10 micrometer, more preferably larger than 30 micrometer, even more preferably larger than 50 micrometer, and/or the largest dimension in a cross section of said flow cell and/or microfluidic system is smaller than 5000 micrometer, more preferably smaller than 3000 micrometer, even more preferably smaller than 2500 micrometer. In a preferred embodiment, said microfluidic system is attached on a substrate, as this is easy manufacturable and provides stability to the microfluidic system.

Although it is not necessary, it may be desired that a fluid flow is present in at least one of the fluidic systems. This allows sampling of the contents of the reactor in time and monitoring of different samples to obtain a better knowledge of the state and/or reactions of the reactor. A fluid flow may be present due to natural phenomenon such as convection, conduction or radiation, by density or pressure differences induced by e.g. the reactions taking place in the reactor or heat gradients, by gravity, etc. If a fluid flow is desired, but is not occurring spontaneously or if the flow needs to be controlled, one or more pumping systems may be connected to the fluidic systems in order to induce a flow in said systems. Therefore, in a preferred embodiment, the fluid microscope system of the present invention comprises at least one pumping system connected to one or more fluidic systems and capable of inducing a fluid flow in said fluidic systems.

The fluid microscope system of the present invention has the advantage of non-destructively monitoring the contents of a reactor. Thereby, it is possible to re-introduce the samples which are observed in the DHM to the reactor. Therefore, in a preferred embodiment, at least one fluidic system forms a closed circuit between one of said reactor and said DHM and back to said reactor, i.e. said fluidic system is capable of guiding fluid from said reactor to said DHM and back. In some set-ups, it may be beneficial to lead observed samples to another reactor. Therefore, in a preferred embodiment, the system of the present inventions comprises at least one fluidic system whereby said fluidic system forms a circuit between said reactor and said DHM and another reactor, i.e. said fluidic system is capable of guiding fluid from said reactor to said DHM and subsequently to said other reactor. Furthermore, in a preferred embodiment, the system of the present invention comprises at least one fluidic system which forms a circuit between a first reactor and the DHM, and between the DHM to said first and at least one other reactor, whereby said fluidic system preferably comprises a switching mechanism which is capable of selecting first and/or other reactors to be connected to the DHM such that the fluid sample observed by the DHM is guided to the selected reactor, preferably depending on an analysis of said sample. Such a system can be used to separate the contents of a reactor according to pre-defined characteristics.

In a preferred embodiment, the fluid microscope system according to the present invention comprises at least one fluidic system which comprises a reactor attachment system for easily attaching and/or detaching said fluidic system to said reactor, whereby leakage of fluid is prevented. In a more preferred embodiment, said reactor attachment system comprises a screw thread mounted on an outer surface which can be screwed into and out of a corresponding screw thread in an opening of a side or lid of said reactor, hereby sealing said opening, i.e. preventing fluid from escaping the volume created by said reactor and said fluidic system, whereby said reactor attachment system comprises at least two passageways for fluid in-flux and fluid out-flux, hereby allowing transport of fluid from said reactor to said DHM and back via said fluidic system. The reactor attachment system can be such that the fluidic system can be connected to a reactor from the top, the side, the bottom or a combination thereof.

In a preferred embodiment, at least one fluidic system comprises a fluid-tight flexible part which, when compressed, pulled and/or pushed results in a fluid flow in said fluidic system. As such, a fluid flow can be induced in the fluidic system without a high risk of leaks and without contamination of the actuator of the flow. In a more preferred embodiment, the fluid microscope system of the present invention comprises a pumping system connected to said fluidic system, capable of pulling and/or pushing said fluid-tight flexible part, thereby inducing a fluid flow in said fluidic system.

In a preferred embodiment, said fluid microscope system comprises a pumping system which comprises a stepwise pump, capable of inducing a stepwise fluid flow in a fluidic system to which said stepwise pump is connected. A stepwise fluid flow may be desired when the DHM is e.g. desired to perform scans which take a certain amount of time. In a stepwise flow, the fluid sample may remain stationary for at least a part of the pumping cycle. During this stationary phase, the DHM may scan or observe the sample over a large area.

In a preferred embodiment, the present invention provides a fluid microscope system as described above, whereby at least one pumping system comprises a continuous pump, capable of inducing a continuous fluid flow in a fluidic system to which said continuous pump is connected. In a more preferred embodiment, said pump is a peristaltic pump. A continuous flow may result in a higher throughput and therefore a faster analysis or better monitoring of the processes in the reactor and fluidic system. Furthermore, due to its fast acquisition time, a DHM is capable of acquiring high-quality holographic images of a sample, even if a continuous flow is present in said sample.

In a further aspect, the present invention provides a tube for a fluidic system of a fluid microscope system as disclosed in this document, preferably comprising a part which is at least partially transparent for illumination means of a DHM of said fluid microscope system for obtaining phase information of a fluid sample in said tube, whereby said at least partially transparent part preferably has a shape suitable for said DHM, preferably a slab-like shape, more preferably a shape comprising two parallel transparent sides, preferably when said DHM works in transmission mode, and/or whereby said at least partially transparent part preferably comprises at least one flat side preferably when said DHM works in reflection mode.

In a preferred embodiment, the present invention provides a tube as described above, whereby said tube is autoclavable, i.e. resistant to temperatures and pressures typically used in a an autoclave to sterilize the tube.

In a preferred embodiment, the present invention provides a tube as described above, whereby said part comprises a flow cell and/or a microfluidic system. Such tube offers the benefits of a flow cell and/or microfluidic system as described previously in this document.

In a further aspect, the present invention provides a package system comprising a tube as described above, and a package for protecting said tube. This allows for an easy handling of the tube when it is transported. The tube in a fluid microscope system such as described in this text may be exchangeable and therefore it should be easily deliverable to the user.

In a preferred embodiment, the present invention provides a package system as described above, whereby said package encloses said tube, thereby protecting said tube against external contamination. In this way, a tube which was sterilized before packaging, remains sterile.

In a preferred embodiment, the present invention provides a package system as described above, whereby said tube is sterile in order to replace another tube in a fluid microscope system as described in this text, hereby reducing the risk of contamination of the content of the reactors.

In yet a further aspect, the present invention provides a fluidic system for a fluid microscope system as disclosed in this document, preferably comprising one or more tubes comprising a part which is at least partially transparent for illumination means of a DHM of said fluid microscope system, whereby preferable the fluidic system comprises one or more components which are separated from fluid from said reactor, whereby preferably said fluidic system is capable of forming a closed circuit between said reactor and said DHM, i.e. said fluidic system is capable of guiding fluid from said reactor to said DHM and back, whereby alternatively said fluidic system is capable of forming a circuit between said reactor and said DHM and another reactor, i.e. said fluidic system is capable of guiding fluid from said reactor to said DHM and subsequently to said other reactor, whereby preferably said fluidic system comprises a reactor attachment system for easily attaching and/or detaching said fluidic system to a reactor, whereby leakage of fluid is prevented, whereby more preferably said reactor attachment system comprises a screw thread mounted on an outer surface which can be screwed into and out of a corresponding screw thread in an opening of a side or lid of said reactor, hereby sealing said opening, i.e. preventing fluid from escaping the volume created by said reactor and said fluidic system, whereby said reactor attachment system comprises at least two passageways for fluid in-flux and fluid out-flux, hereby allowing transport of fluid from said reactor to said DHM and back via said fluidic system.

In yet another aspect, the present invention provides an assembly of a fluid microscopic system, one or more fluidic systems, one or more tubes and/or one or more pumps as disclosed in this text, capable of being connected to one or more reactors or containers.

The invention is further described by the following non-limiting examples which further illustrate the invention, and are not intended to, nor should they be interpreted to, limit the scope of the invention.

EXAMPLES

FIG. 1 illustrates a setup whereby a fluid microscope system is connected to one reactor, such as a bio-reactor. The fluid microscope system (1) comprises a DHM (2) and a fluidic system (3) which provides a fluidic connection between the DHM and a reactor (4). The fluidic system (3) is connected to the reactor (4) with a fluid-tight arrangement (5). The fluidic system (3) may comprises a number of bendable tubes inside a bendable cover, as illustrated in e.g. FIG. 3, whereby a closed fluidic circuit is formed between the reactor and the DHM, or it may comprise only one tube. Such fluidic systems (3) provide an easy connection between the reactor (4) and the DHM (2), even when it is located a certain distance away. The fluidic system (3) of FIG. 1 comprises a tube comprising a cartridge (6) which is at least partially transparent for the illumination means of the DHM and has a shape comprising two parallel transparent sides, e.g. top and bottom. This part can be easily introduced in a sample scanning system (7), which in FIG. 1 comprises an input port for only one fluidic system. The cartridge (6) may be attached to the DHM by a simple connecting mechanism such as snap-fit connectors on the sides of the cartridge (6).

Figure 2:
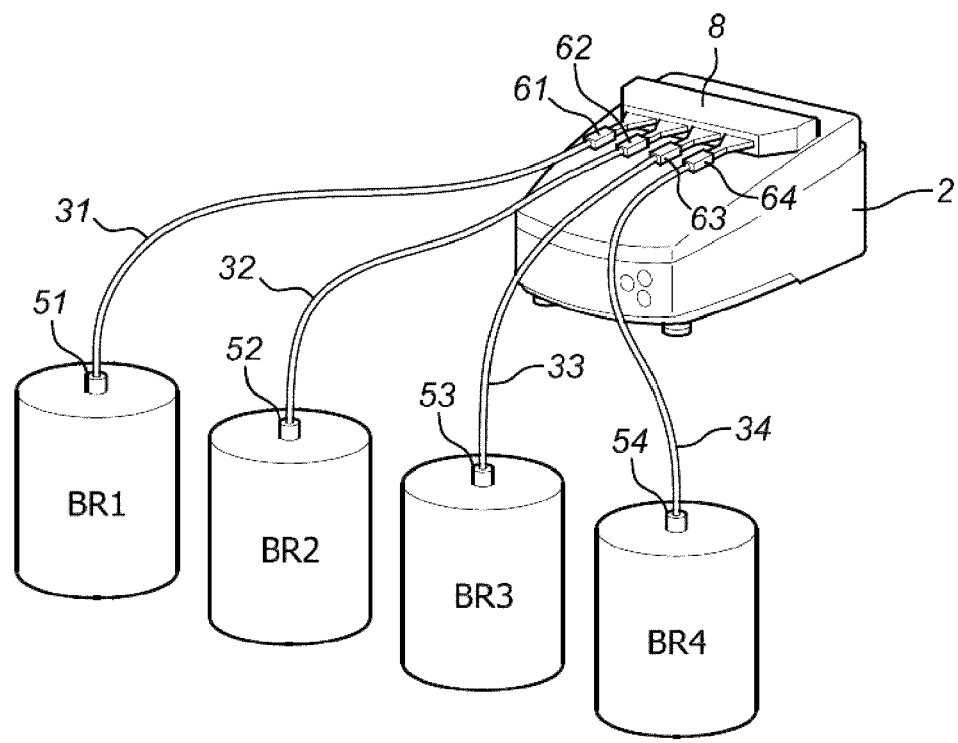
FIG. 2 shows a set-up with a fluid microscopic system according to the present invention in combination with four reactors or containers.

FIG. 2 shows a set-up with a fluid microscopic system according to the present invention in combination with four reactors or containers. Four reactors, e.g. bio-reactors (BR1, BR2, BR3, BR4) are connected to a fluid microscope system comprising four fluidic systems (31-34) which may form separate and closed fluidic circuits between the respective reactors (BR1-BR4) and the DHM (2). The fluidic systems (31-34) comprise reactor attachment systems (51-54) for easy and fluid-tight connection of the fluidic systems to the reactors (BR1-BR4). Furthermore, the fluidic systems (31-34) are connected to a multiple-sample scanning system (8) with in this case, at least four input ports for fluidic systems. The multiple-sample scanning system (8) may comprise an optical system comprising e.g. rotatable mirrors, with which one can change the optical path of the illumination beam of the illumination means of the DHM, in order to, preferably subsequently, scan, monitor or observe the samples in the transparent parts of the cartridges (61-64) of tubes of the different fluidic systems (31-34). The settings of the DHM and/or multiple-sample scanning system, such as scanning speed, scanning time, scanning time per sample, etc. may be controlled by an internal or external server or control unit.

Figure 3:
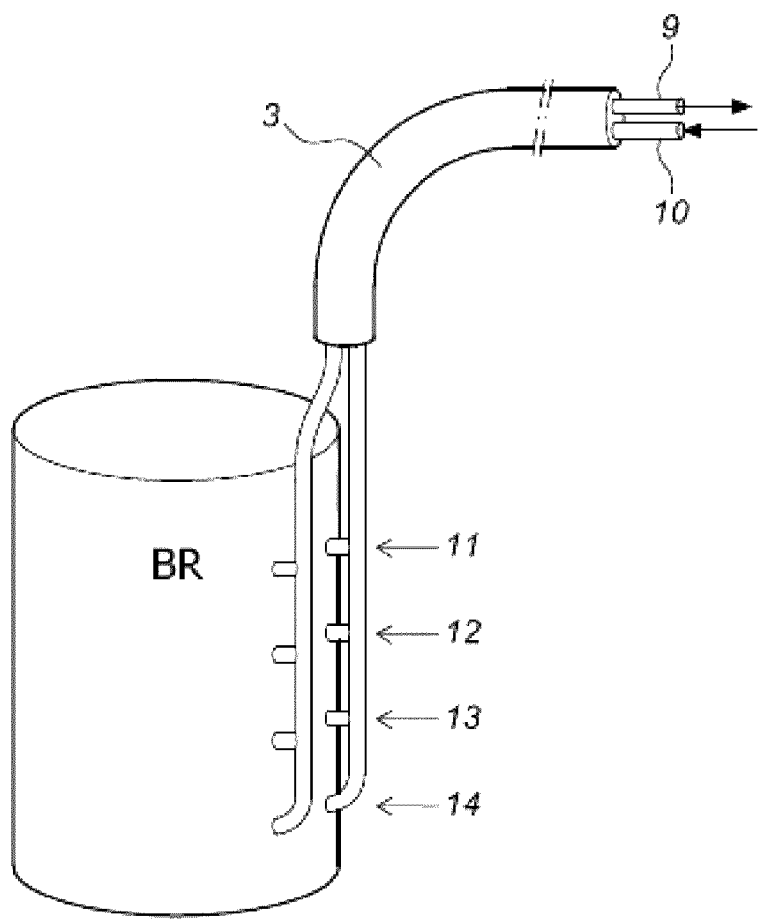
FIGS. 3 and 4 show two different connections of a fluidic system according to the present invention with a reactor.
Figure 4:
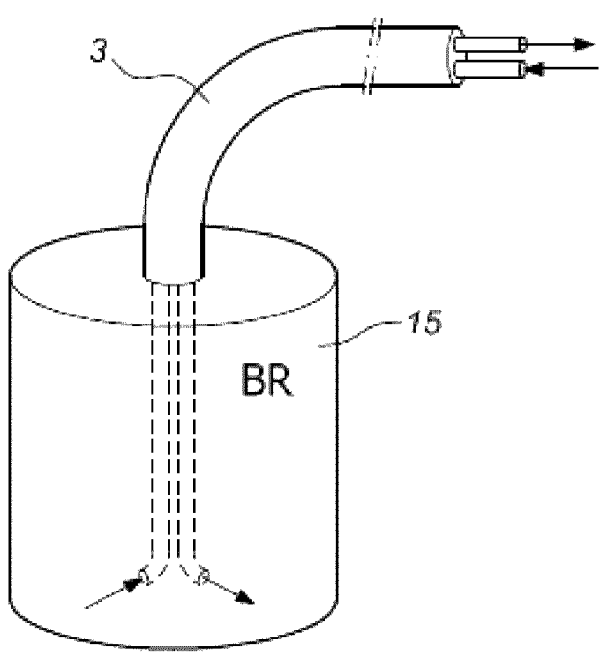

FIGS. 3 and 4 show two different connections of a fluidic system according to the present invention with a reactor. In FIG. 3, a fluidic system comprises two tubes for extraction (9) and return (10) of the fluid from and to the reactor (BR) and this at different heights (11-14). Alternatively, one could connect separate fluidic systems at the different heights (11-14) whereby one could obtain holographic information about the state and processes of the contents of the reactor (BR) at different heights. Such a set-up could be interesting to monitor a heterogeneous fluid, e.g.

a suspension of heterogeneous objects whereby the denser and/or heavier objects may be located closer to the bottom. In FIG. 4, a fluidic system (3) is seen to be connected to a reactor (BR) via the top (15). In case the fluid in the reactor (BR) is a liquid, or even a heavy gas, the fluid-tightness of the connection between fluidic system and reactor need not always be ensured in this set-up, which would facilitate easy attachment and detachment of the reactor to and from the fluid microscope system.

Figure 5:
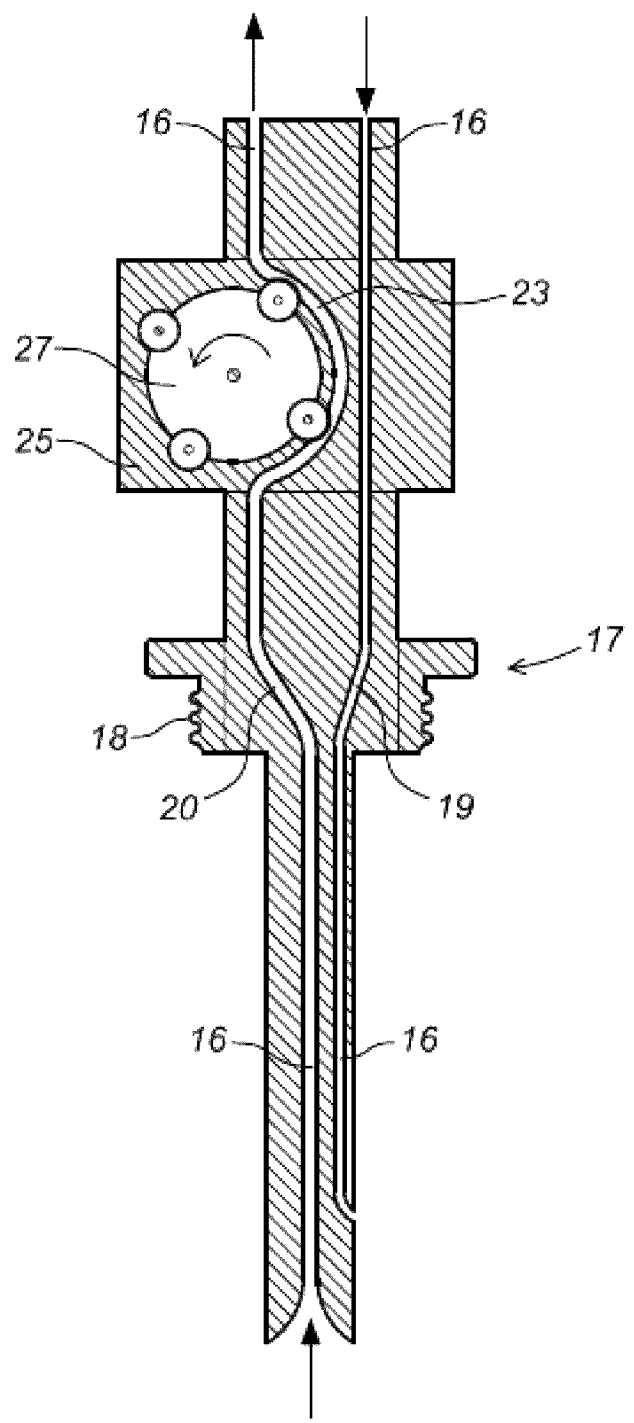
FIG. 5 shows an embodiment of part of a fluid microscope system according to the present invention.

FIG. 5 shows an embodiment of part of a fluid microscope system according to the present invention. The system comprises a fluidic system comprising a set of tubes (16) for extraction and return of fluid. The fluidic system comprises a reactor attachment system (17) for easily attaching and/or detaching said fluidic system to said reactor, whereby leakage of fluid is prevented, whereby said reactor attachment system comprises a screw thread (18) mounted on an outer surface which can be screwed into and out of a corresponding screw thread in an opening of a side or lid of said reactor, hereby sealing said opening, i.e. preventing fluid from escaping the volume created by said reactor and said fluidic system, whereby said reactor attachment system comprises at least two passageways for fluid in-flux (19) and fluid out-flux (20), hereby allowing transport of fluid from said reactor to said DHM and back via said fluidic system. The fluidic system also comprises a fluid-tight flexible part (23) which, when peristaltically compressed results in a continuous peristaltic fluid flow in said fluidic system. In FIG. 5, this flexible part is illustrated in a specific position of the peristaltic pump (27) of the pumping system (25), capable of inducing a fluid flow in said fluidic systems.

Figure 6:
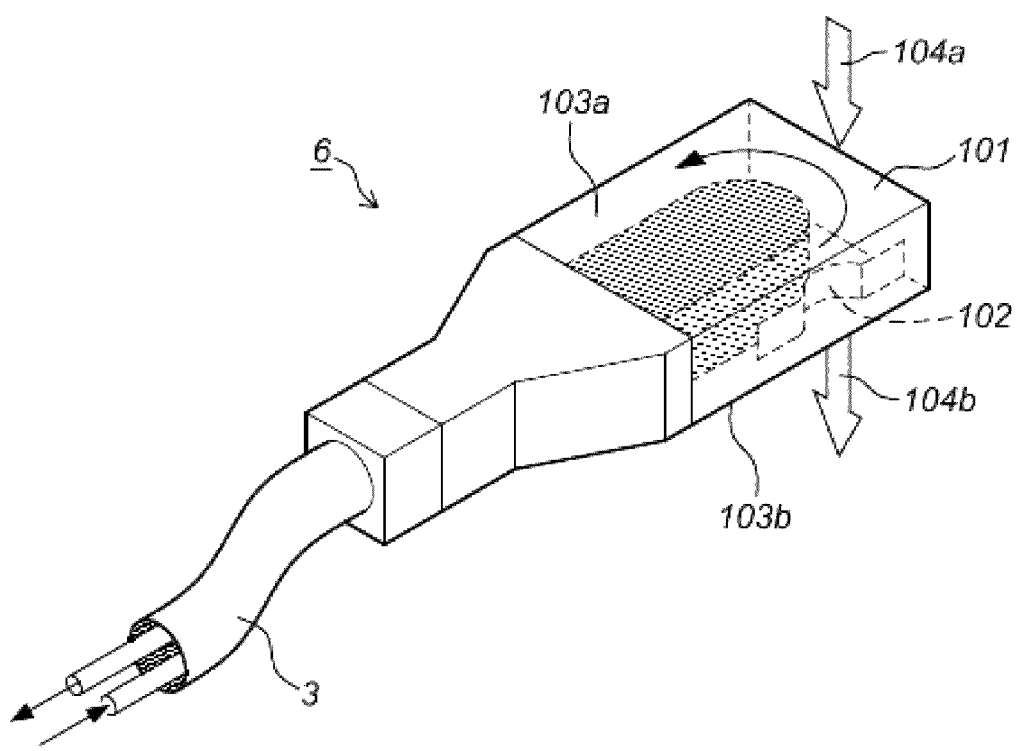
FIG. 6 shows a detail of the cartridge of a tube which is at least partially transparent for the illumination means of the DHM and has a shape comprising two parallel transparent sides, e.g. top and bottom.

FIG. 6 shows a detail of the cartridge (6) of a tube which is at least partially transparent for the illumination means of the DHM and has a shape comprising two parallel transparent sides, e.g. top (103a) and bottom (103b). The cartridge (6) comprises a transparent part (101) through which a fluid can flow. The cartridge (6) can be easily attached to and detached from a DHM (2) or to a multiple-sample scanning system (8) due to a connector (102) such as a snap-fit connector. When the cartridge (6) is plugged into a DHM or scanning system, the parallel transparent sides are placed perpendicular to and into the illumination beam (104a, 104b). The illumination beam before interaction with the sample (104a) can thus illuminate the sample through the top side (103a) and the illumination beam after interaction with the sample (104a) eventually gives rise to a holographic image obtained by the recording means of the DHM, e.g. a differential DHM.

Figure 7A:
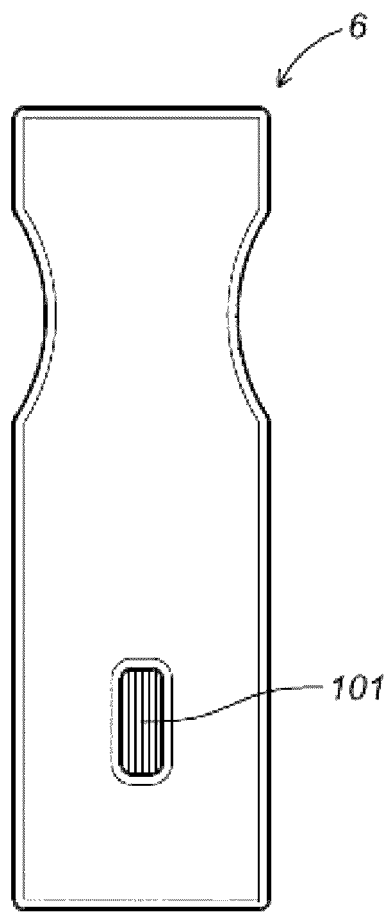
FIGS. 7a and 7b show a different type of cartridge from the front (FIG. 7a) and the back (FIG. 7b).
Figure 7B:
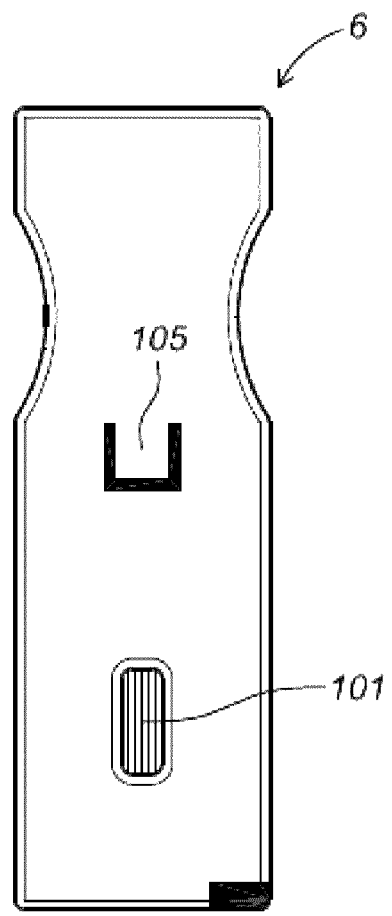

FIGS. 7a and 7b show a different type of cartridge (6) from the front (FIG. 7a) and the back (FIG. 7b). The cartridge comprises transparent parts (101). In this case, the transparent part (101) is a flow cell whereby the diameter varies along the width. A snap-fit connector (105) is mounted on the back of the cartridge. The cartridge is 75 mm long, 25 mm wide and 8 mm thick.

Figure 8A:
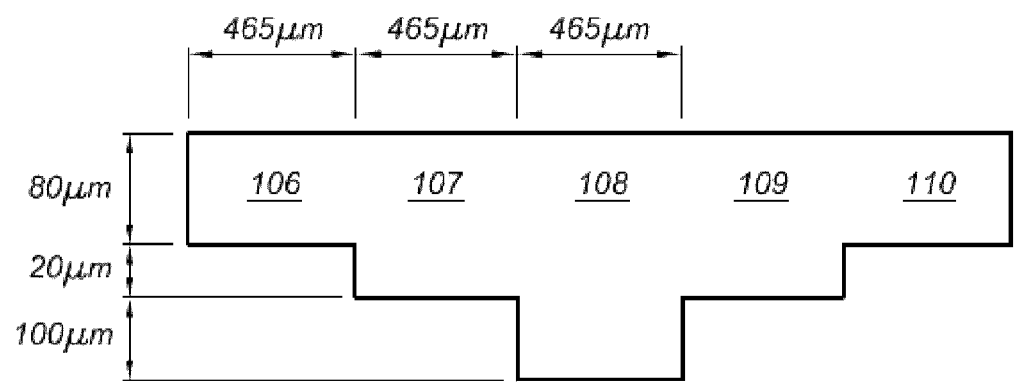
FIGS. 8a and 8b show a cross section (FIG. 8a) of a flow cell and a top view (FIG. 8b) of how a flow cell is inserted in a fluidic system.
Figure 8B:
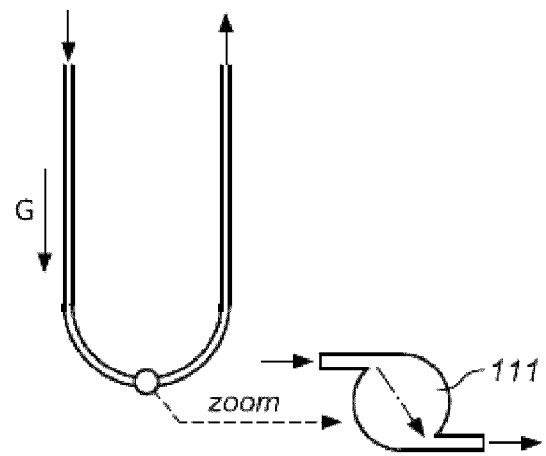

FIGS. 8a and 8b show a cross section (FIG. 8a) of a flow cell and a top view (FIG. 8b) of how a flow cell is inserted in a fluidic system. The cross section comprises two narrow parts (106, 110) which are 80 micrometer high and 465 micrometer wide, two intermediate parts (107, 109) which are 100 micrometer high and 465 micrometer wide and a central part (108) which is 200 micrometer high and 465 micrometer wide. Depending on the concentration of the objects suspended in the fluid medium, the DHM can be made to obtain images from either the narrow parts, the intermediate parts or the central part. The flow cell shown in top view in FIG. 8b has a widened part (111) which i.a. results in a reduction of the flow velocity.

Figure 9:
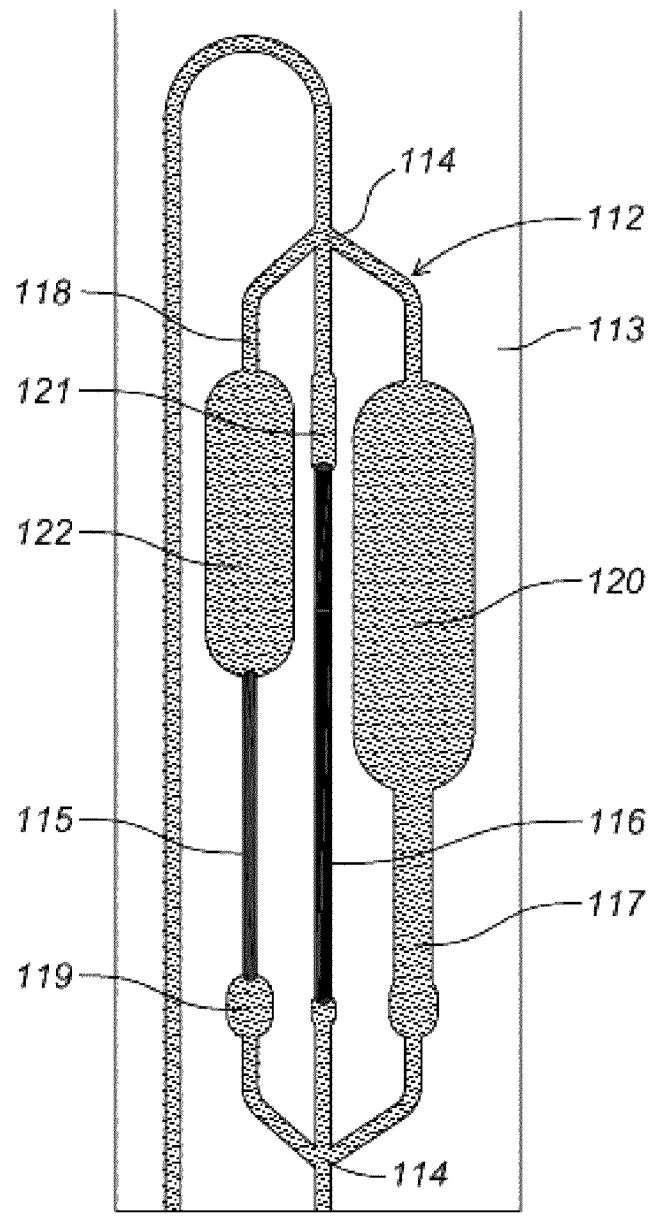
FIG. 9 shows a microfluidic system comprising transparent sides and mounted on a substrate.

FIG. 9 shows a microfluidic system (112) comprising transparent sides and mounted on a substrate (113). The system (112) comprises a branching (114) of the tube into three tubes of different widths and heights. A left branch (115) is 220 micrometer wide and 100 micrometer deep, a middle branch (116) is 300 micrometer wide and 100 micrometer deep, and a right branch (117) is 600 micrometer wide and 50 micrometer deep. The fluid may flow from position (118) in the direction of position (119) or vice versa. Also present are a number of reservoirs in each branch (120, 121, 122) whose volumes depend on the branches and which help to regulate or control the fluid flow in the branches.

Figure 10:
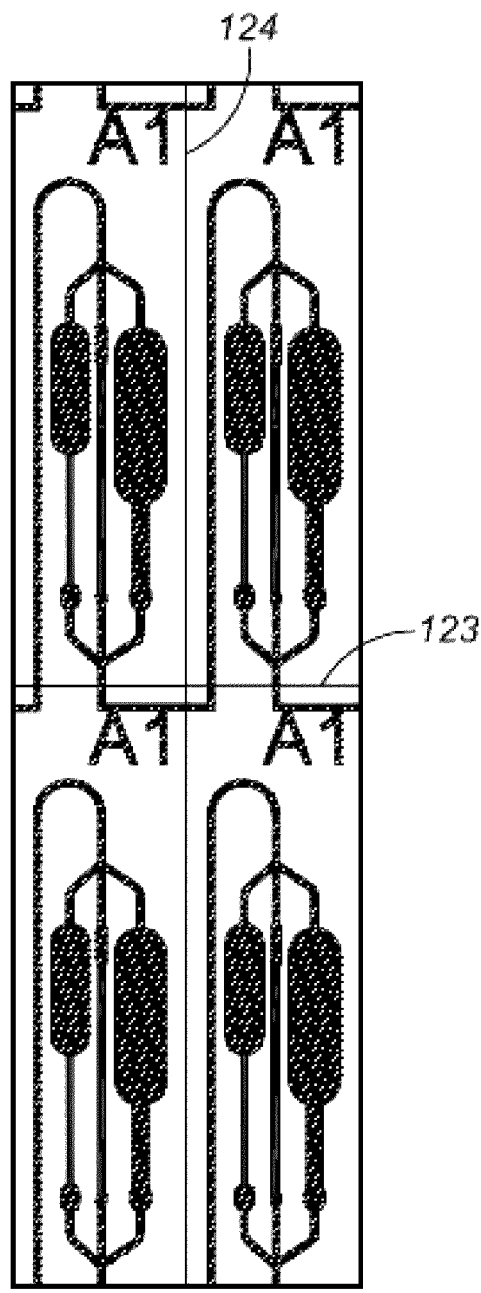
FIG. 10 illustrates how a large number of microfluidic systems may be easily manufactured on one substrate.

FIG. 10 illustrates how a large number of microfluidic systems may be easily manufactured on one substrate. Shown is a subset of four microfluidic systems (112) as in FIG. 9 on one substrate, but it is clear that a very large number may be manufactured on the same substrate. Afterwards, the substrate may be cut along the indicated lines (123, 124) to separate the microfluidics systems.

Figure 11:
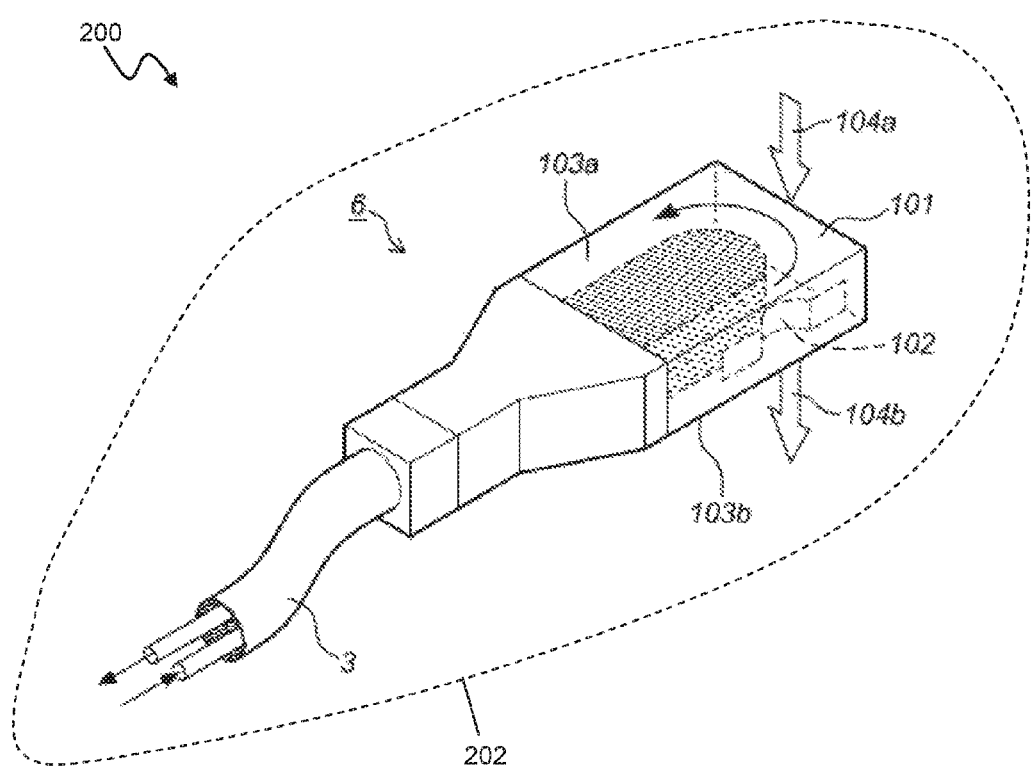
FIG. 11 illustrates a package system.

FIG. 11 illustrates a package system (200) comprising a tube for a fluidic microscope system as described herein, wherein the tube comprises a cartridge as illustrated in FIG. 6 and further comprises a package (202) for protecting the tube.

It is supposed that the present invention is not restricted to any form of realization described previously and that some modifications can be added to the presented example of fabrication without reappraisal of the appended claims.

What is claimed is:

1. A fluid microscope system for analyzing and/or monitoring the contents of one or more fluid-based reactors or canalizations such as bio-reactors, micro-reactors, brewing reactors, water supply systems or sewer systems, comprising:
   a digital holographic microscope (DHM) capable of obtaining phase information of a fluid sample and comprising illumination means; and
   one or more fluidic systems connected to said reactors and to said DHM, capable of guiding fluid from said reactors to said DHM, wherein at least one fluidic system comprises one or more tubes which may come in direct contact with fluid from said reactor, characterized in that at least one tube comprises a part which is at least partially transparent for the illumination means of said DHM for obtaining holographic information of said fluid sample, wherein said tube comprises a flow cell and/or a microfluidic system, said flow cell and/or microfluidic system comprising a cross section in which the height varies along the cross section and the flow cell and/or microfluidic system is configured for obtaining a DHM image at two or more different heights of the cross-section.

2. The fluid microscope system according to claim 1, wherein said tube comprises a part which is at least partially transparent for the illumination means of said DHM and which has a shape suitable for said DHM.

3. The fluid microscope system according to claim 1, wherein said tube comprises a microfluidic system, said microfluidic system comprising a branching of said tube in multiple tubes of different cross sections, diameters, heights and/or widths.

4. The fluid microscope system according to claim 3, comprising transparent sides and being mounted on a substrate.

5. The fluid microscope system according to claim 4, wherein said branches comprise a number of reservoirs whose volumes depend on the branches and which help to regulate or control the fluid flow in the branches.

6. The fluid microscope system according to claim 1, comprising at least one pumping system connected to said one or more fluidic systems and capable of inducing a fluid flow in said fluidic systems.

7. The fluid microscope system according to claim 6, wherein said at least one pumping system comprises a peristaltic pump, capable of inducing a continuous fluid flow in a fluidic system to which said peristaltic pump is connected.

8. The fluid microscope system according to claim 1, wherein at least one fluidic system forms a closed circuit between one of said reactor and said DHM and back to said reactor.

9. The fluid microscope system according to claim 1, wherein at least one fluidic system comprises a reactor attachment system for easily attaching and/or detaching said fluidic system to said reactor, whereby leakage of fluid is prevented.

10. The fluid microscope system according to claim 1, wherein at least one fluidic system comprises a fluid-tight flexible part which, when compressed, pulled and/or pushed results in a fluid flow in said fluidic system.

11. The fluid microscope system according to claim 10, comprising a pumping system with a pump connected to said fluidic system, capable of compressing, pulling and/or pushing said fluid-tight flexible part, thereby inducing a fluid flow in said fluidic system.

12. A tube for a fluidic system of a fluid microscope system according to claim 1, comprising a part which is at least partially transparent for illumination means of a digital holographic microscope (DHM) of said fluid microscope system, wherein said tube comprises a flow cell and/or a microfluidic system, said flow cell and/or microfluidic system comprising a cross section in which the height varies along the cross section and the flow cell and/or microfluidic system is configured for obtaining a DHM image at two or more different heights of the cross-section.

13. The tube according to claim 12, wherein said tube is autoclavable.

14. A package system comprising a tube according to claim 12 and a package for protecting said tube.

15. The package system according to claim 14, wherein said package encloses said tube, thereby protecting said tube against external contamination.

16. The package system according to claim 14, wherein said tube is sterile.

17. A fluidic system for a fluid microscope system according to claim 1, comprising one or more tubes comprising a part which is at least partially transparent for illumination means of a DHM of said fluid microscope system, wherein said tube comprises a flow cell and/or a microfluidic system, said flow cell and/or microfluidic system comprising a cross section in which the height varies along the cross section and the flow cell and/or microfluidic system is configured for obtaining a DHM image at two or more different heights of the cross-section.

18. The fluid microscope system according to claim 1, wherein the narrowest dimension in a cross section of said flow cell and/or microfluidic system is larger than 10 micrometer, more preferably larger than 30 micrometer, even more preferably larger than 50 micrometer, and/or the largest dimension in a cross section of said flow cell and/or microfluidic system is smaller than 5000 micrometer, more preferably smaller than 3000 micrometer, even more preferably smaller than 2500 micrometer.

19. The fluid microscope system according to claim 1, wherein said tube comprises a flow cell, said flow cell comprising a widened part for reducing the flow velocity.

20. The fluid microscope system according to claim 1, wherein said tube comprises a flow cell, said flow cell comprising two narrow parts, two intermediate parts and a central part.

* * * * *

UNITED STATES PATENT AND TRADEMARK OFFICE
CERTIFICATE OF CORRECTION

PATENT NO. : 9,904,248 B2
APPLICATION NO. : 14/429616
DATED : February 27, 2018
INVENTOR(S) : Philip Mathuis Page 1 of 1

It is certified that error appears in the above-identified patent and that said Letters Patent is hereby corrected as shown below:

On the Title Page

Item (57), Abstract at Line 6, Change "systems" to --systems,--.

In the Specification

In Column 3 at Line 46, Change "Fundation," to --Foundation,--.

In Column 4 at Line 18, Change ""Saptiotemporal" to --"Spatiotemporal--.

In Column 16 at Line 42, After "in" delete "a".

In Column 18 at Lines 24-32, Below "e.g." delete "a suspension of heterogeneous objects whereby the denser and/or heavier objects may be located closer to the bottom. In FIG. 4, a fluidic system (3) is seen to be connected to a reactor (BR) via the top (15). In case the fluid in the reactor (BR) is a liquid, or even a heavy gas, the fluid-tightness of the connection between fluidic system and reactor need not always be ensured in this set-up, which would facilitate easy attachment and detachment of the reactor to and from the fluid microscope system." and insert the same on Column 18, Line 23, as a continuation of the same paragraph.

Signed and Sealed this
Nineteenth Day of June, 2018

Andrei Iancu
*Director of the United States Patent and Trademark Office*